United States Patent
Nelson et al.

(10) Patent No.: US 9,845,277 B2
(45) Date of Patent: Dec. 19, 2017

(54) METHOD OF RECOVERING ACETONE AND A PLANT FOR RECOVERING THE SAME

(71) Applicant: SABIC Global Technologies B.V., Bergen op Zoom (NL)

(72) Inventors: Mark Erik Nelson, Mt. Vernon, IN (US); Ahmed Abouelfetouh Youssef, Mt. Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/421,793

(22) Filed: Feb. 1, 2017

(65) Prior Publication Data

US 2017/0240496 A1    Aug. 24, 2017

Related U.S. Application Data

(60) Provisional application No. 62/298,638, filed on Feb. 23, 2016.

(30) Foreign Application Priority Data

Feb. 25, 2016 (EP) .................... 16157250

(51) Int. Cl.
| | |
|---|---|
| *C07C 45/80* | (2006.01) |
| *B01D 11/00* | (2006.01) |
| *B01J 19/00* | (2006.01) |
| *B01D 11/04* | (2006.01) |
| *B01J 19/24* | (2006.01) |
| *C07C 37/20* | (2006.01) |
| *C07C 45/82* | (2006.01) |

(52) U.S. Cl.
CPC .......... *C07C 45/80* (2013.01); *B01D 11/0488* (2013.01); *B01J 19/24* (2013.01); *C07C 37/20* (2013.01); *C07C 45/82* (2013.01); *B01J 2219/24* (2013.01)

(58) Field of Classification Search
CPC ......... C07C 45/00; C07C 45/82; C07C 37/20; B01D 11/0488; B01J 19/24
USPC ........................................ 568/411
See application file for complete search history.

(56) References Cited

U.S. PATENT DOCUMENTS

| | | |
|---|---|---|
| 8,143,456 B2 | 3/2012 | Young et al. |
| 9,255,053 B2 | 2/2016 | Palmer et al. |
| 2004/0249224 A1 | 12/2004 | Kumbhar et al. |
| 2008/0281129 A1 | 11/2008 | Palmer |
| 2010/0105960 A1 | 4/2010 | Evitt et al. |
| 2012/0310014 A1 | 12/2012 | Palmer et al. |

FOREIGN PATENT DOCUMENTS

| | | |
|---|---|---|
| JP | 3775832 B2 | 4/1997 |
| WO | 2009032552 A2 | 3/2009 |

OTHER PUBLICATIONS

Extended Search Report for European Patent Application No. 16157250.8; dated Feb. 25, 2016; dated Jul. 28, 2016; 3 pages.
Noureldin et al.; "Global energy targets and optimal operating conditions for waste energy recovery in Bisphenol-A plant"; Applied Thermal Engineering 26 (2006); pp. 374-381.

*Primary Examiner* — Sikarl Witherspoon
(74) *Attorney, Agent, or Firm* — Cantor Colburn LLP

(57) ABSTRACT

In an embodiment, a method of recovering acetone comprises separating a bisphenol A stream into a bisphenol A product stream and an extraction stream comprising unreacted acetone; recovering the unreacted acetone in a recovery section of the bisphenol A production facility and forming a bisphenol A plant acetone recovery stream comprising methanol and a recovered acetone; introducing the bisphenol A plant acetone recovery stream to a phenol purification plant; and purifying the bisphenol A plant acetone recovery stream in the phenol purification plant to form an acetone product stream. The acetone product stream can comprise a reduced amount of methanol as compared to the bisphenol A plant acetone recovery stream.

19 Claims, 2 Drawing Sheets

US 9,845,277 B2

METHOD OF RECOVERING ACETONE AND A PLANT FOR RECOVERING THE SAME

CROSS REFERENCE TO RELATED APPLICATION

This application claims the benefit of U.S. Provisional Patent Application Ser. No. 62/298,638 filed Feb. 23, 2016 and to European Application 16157250 filed Feb. 25, 2016. The related applications are incorporated herein in their entirety by reference.

TECHNICAL FIELD

This disclosure relates to a method of recovering acetone and a plant for recovering the same.

BACKGROUND

Bisphenol A (BPA) is a high production volume compound with a world-wide estimated annual production of over 2 million tons. The demand for this compound is primarily due to its use as a monomer in the production of many high commodity materials such as epoxies and polycarbonates. The general process by which BPA is produced involves the condensation reaction of acetone with two equivalents of phenol in the presence of an acid catalyst or a sulfonated polystyrene resin. This reaction is often performed in an excess of phenol in order to help ensure full condensation. As a result, in a BPA production plant, the product stream comprises the excess phenol that can be separated from the product BPA. The separated phenol comprises an amount of unreacted acetone. This excess unreacted phenol and unreacted acetone can be recovered and either recycled back to the BPA production plant or used for a different process.

There remains a need in the art for a process, which can more efficiently recover acetone from a BPA plant.

BRIEF SUMMARY

Disclosed herein is a method of recovering and purifying acetone and a plant for recovering the same.

In an embodiment, a method of recovering acetone comprises reacting phenol and acetone in the presence of a catalyst in a BPA reactor to produce a bisphenol A stream comprising bisphenol A; separating the bisphenol A stream into a product bisphenol A stream and an extraction stream comprising an unreacted acetone; separating the extraction stream into an extraction top outlet stream and an extraction bottom outlet stream in an acetone extraction column; separating the extraction bottom outlet stream in an acetone stripper column in the presence of steam to form a stripper top outlet stream and a stripper bottom outlet stream comprising water; separating the extraction top outlet stream in a solvent recovery column to form a recovery top outlet stream and a recovery bottom outlet stream; separating one or both of the recovery top outlet stream and the stripper top outlet stream in a decanter to form an organic decanter stream and an aqueous decanter stream; forming a bisphenol A plant acetone recovery stream comprising at least a portion of one or more of the extraction top outlet stream, the stripper top outlet stream, the aqueous decanter stream, and the recovery top outlet stream; introducing the bisphenol A plant acetone recovery stream to a phenol purification plant, wherein the bisphenol A plant acetone recovery stream comprises methanol and a recovered acetone; and purifying the bisphenol A plant acetone recovery stream to form an acetone product stream.

In another embodiment, a method of purifying a recovered acetone comprises introducing a bisphenol A plant acetone recovery stream to at least one of a preheater, a splitter column, and a first acetone column of a phenol purification plant; wherein the bisphenol A plant acetone recovery stream comprises methanol and the recovered acetone; heating a preheater inlet stream comprising cumene, phenol, and acetone in the preheater to form a splitter inlet stream; separating the splitter inlet stream comprising the cumene, the phenol, and the acetone into a splitter top outlet stream comprising the acetone and the cumene and a splitter bottom outlet stream comprising the phenol in the splitter column; separating the splitter top outlet stream in the first acetone column into a first top stream and a first bottom stream; separating the first bottom stream in a second acetone column into a second bottom stream and an acetone product stream comprising a purified acetone.

In a further embodiment, an integrated system for purifying acetone comprises an acetone extraction column comprising a first extraction inlet, a top extraction outlet, and a bottom extraction outlet; an acetone stripper column comprising comprise a stripper inlet, a steam stripper inlet, a top stripper outlet, and a bottom stripper outlet; wherein the bottom extraction outlet is in fluid communication with the stripper inlet; a decanter comprising a decanter inlet, an aqueous decanter outlet, and an organic decanter outlet; wherein one or both of the top solvent recovery outlet and the top stripper outlet is in fluid communication with the decanter inlet; and an optional solvent recovery column comprising a first solvent recovery inlet, a second solvent recovery inlet, a top solvent recovery outlet, and a bottom recovery outlet; wherein, if present, the top extraction outlet is in fluid communication with the first solvent recovery inlet; the organic decanter outlet is in fluid communication with one or both of the second solvent recovery inlet and a second extraction inlet of the acetone extraction column; and wherein the top extraction outlet, the top stripper outlet, the aqueous decanter outlet, top solvent recovery outlet, or a combination comprising at least one of the foregoing is in fluid communication with a stream of a phenol purification system; wherein the phenol purification system is configured to recover an acetone product stream.

The above described and other features are exemplified by the following figures and detailed description.

BRIEF DESCRIPTION OF THE DRAWINGS

Refer now to the figures, which is an exemplary embodiment, and wherein the like elements are numbered alike. It is noted that the streams entering each of the respective columns can enter as separate streams or as combined streams and that the figures are merely illustrations of embodiments of the present method.

DETAILED DESCRIPTION

Acetone recovered from a typical BPA plant generally results in a purified acetone with a high methanol concentration (for example, comprising 0.4 to 2 weight percent (wt %)). It was surprisingly discovered that by purifying the acetone stream from the BPA production facility in an acetone purification section of a phenol production facility (that is not generally known for removing a methanol impurity), the methanol concentration in the acetone product stream could be reduced as compared to the methanol concentration of the bisphenol A plant acetone recovery stream, for example, to an amount of less than or equal to 150 parts per million by weight (ppm) based on the total weight of the acetone product stream. This reduction in methanol in the recovered acetone can be significant as any methanol present in the acetone that gets recycled for use in the BPA production plant, results in a decrease lifetime of the promotor used in the BPA production.

Figure 1:
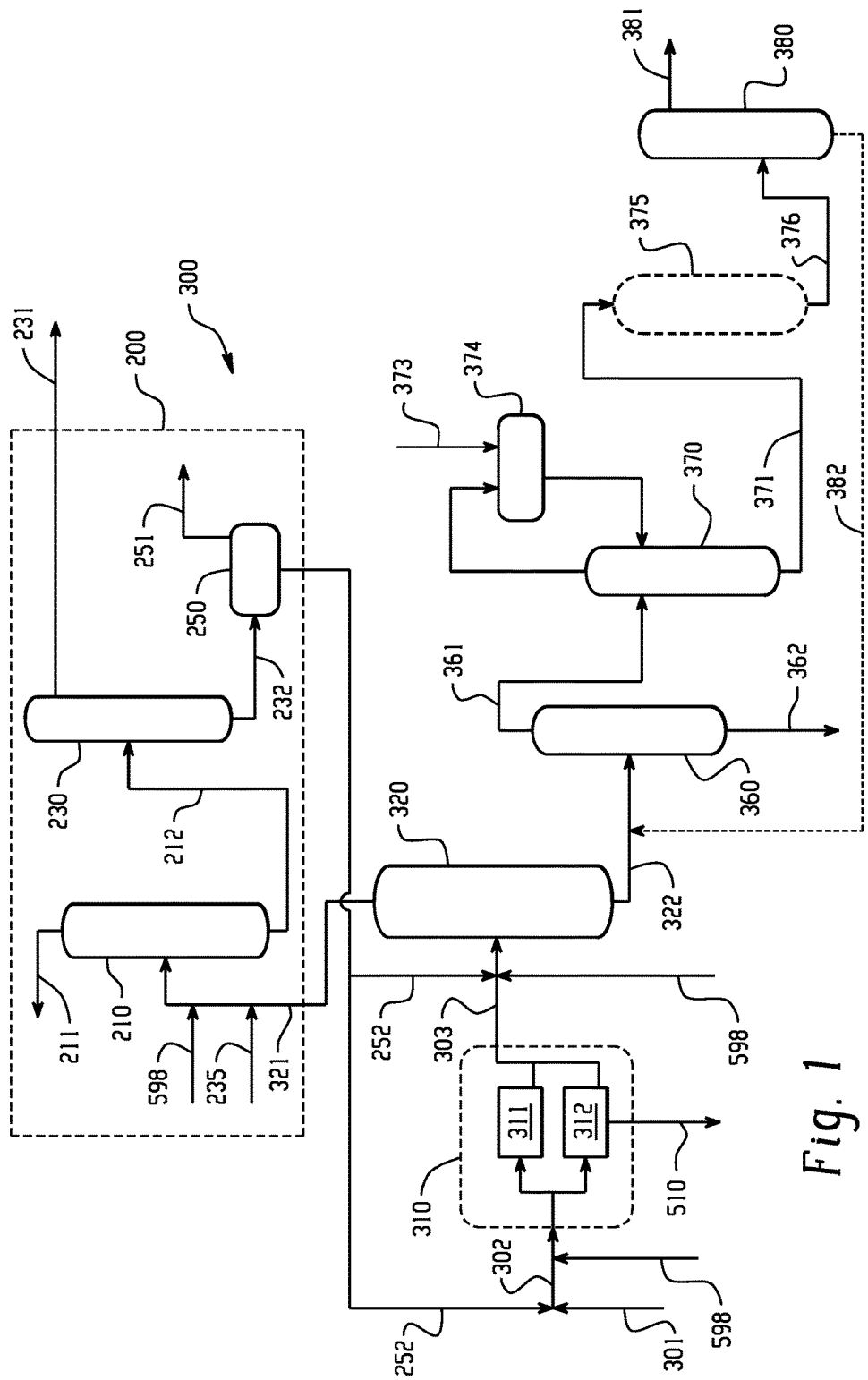
FIG. 1 is a schematic illustration of an embodiment of a phenol and acetone purification system of a phenol production plant.

An example of a reaction to produce phenol is via the cumene process. Here, a reaction mixture of benzene, propylene, and oxygen is reacted to produce a product mixture comprising acetone and phenol. A phenol purification system can be used to purify the product mixture, for example, as illustrated in FIG. 1. FIG. 1 is a schematic illustration of a phenol purification system 300 of a phenol production plant. The phenol purification system 300 can include a feed stream 301 comprising acetone and phenol. The feed stream 301 can further comprise non-phenol compounds from upstream phenol production processes such as water, cumene, dimethylbenzyl alcohol (DMBA), hydroxyacetone (HA), α-methylstyrene (AMS), AMS dimers, acetophenone (AP), acetaldehyde, cumyl phenols, phenolic resins, or a combination including at least one of the foregoing.

The feed stream 301 can be combined with one or both of an acetone purification recycle stream 252 containing phenol recovered from an acetone purification section 200 and BPA plant acetone recovery stream 598 to form a preheater inlet stream 302. The preheater inlet stream 302 can be heated in a preheater 310 by any suitable heating process. For example, preheater 310 can comprise preheater units 311 and 312 that operate in parallel. In this configuration, the preheater 310 can accommodate a higher flowrate while still heating the preheater inlet stream 302 to a desired temperature. It is noted that while it is illustrated that the three streams are combined prior to entering the preheater, the streams can be added in other configurations to the preheater.

The preheater 310 can be in fluid communication with a splitter column 320 via splitter inlet stream 303. Splitter inlet stream 303 can comprise 5 to 50 wt %, specifically, 10 to 40 wt %, more specifically, 20 to 40 wt % acetone. Splitter inlet stream 303 can comprise 20 to 75 wt %, specifically, 30 to 60 wt %, more specifically 40 to 50 wt % phenol. The splitter inlet stream 303 can comprise 0 to 35 wt %, specifically, 5 to 30 wt % of a non-phenol compound. The preheater can be operated such that the splitter inlet stream 303 is heated to a temperature of greater than or equal to 90° C., for example, 90 to 180° C., or 90 to 150° C., or 100 to 135° C. One or both of an acetone purification recycle stream 252 and BPA plant acetone recovery stream 598 can be added to the splitter inlet stream 303 prior to entering the splitter column 320, or can be added separately. The splitter column 320 separates species of the splitter inlet stream 303 into a splitter top outlet stream 321 and a splitter bottom outlet stream 322 based on their volatility (e.g., the tendency of the species to vaporize at a given temperature which is related to the species vapor pressure). The splitter column 320 can include one or more distillation columns. The splitter column 320 can operate at a temperature of 90 to 150 degrees Celsius (° C.), specifically, 100 to 140° C. The splitter column 320 can operate at a pressure of 250 to 450 kilopascal (kPa), specifically, 300 to 400 kPa.

The splitter top outlet stream 321 can contain the high volatility species of the splitter inlet stream 303 including acetone, where, for example, the splitter bottom outlet stream 322 can comprise less than or equal 1 wt % of acetone, or less than or equal to 0.01 wt % of acetone, or 0 wt % of acetone. The splitter top outlet stream 321 can comprise 30 to 70 wt %, specifically, 40 to 60 wt % acetone. The splitter top outlet stream 321 can comprise 10 to 40 wt %, specifically, 15 to 30 wt % cumene. The splitter top outlet stream 321 can comprise 0 to 5 wt %, specifically, 0 to 1 wt % phenol. The splitter top outlet stream 321 can comprise less than or equal to 35 wt %, specifically, 1 to 30 wt % of non-phenol compounds such as α-methylstyrene, water, hydroxyacetone, acetaldehyde, or a combination comprising at least one of the foregoing. The splitter top outlet stream 321 can comprise 0 to 1 wt % of each of the following independently: dimethylbenzyl alcohol, paracumyl phenol, dicumyl phenol, hydroxyacetone, acetophenone, methanol, acetaldehyde, AMS dimer, and 2-methylbenzofuran.

The splitter top outlet stream 321 can be recovered from the top of the splitter column 320 and fed to the acetone purification section 200 where an acetone product stream 231 can be recovered. For example, splitter column 320 can be in fluid communication with first acetone column 210 via the splitter top outlet stream 321 and caustic stream 235 can further be added to a first acetone column 210. First acetone column 210 can form a first top stream 211 and a first bottom stream 212. The first bottom stream 212 can be added to a second acetone column 230 to form a second bottom stream 232 and acetone product stream 231 comprising the purified product acetone.

The second bottom stream 232 can comprise 95 to 100 wt % of all of the methanol added via bisphenol A plant acetone recovery stream 598. The second bottom stream 232 can be separated in a separator 250, for example, in a decanter, to form decanted stream 251 comprising cumene, and an acetone phenol recycle stream 252 that can be added to one or both of the preheater 310 and to the splitter column 320. The acetone product stream 231 can comprise 99.5 to less than 100 wt %, or 99.6 to less than 100 wt %, or 99.7 to less than 100 wt % of acetone. The acetone product stream 231 can comprise less than or equal to 0.5 wt % of water. The acetone product stream 231 can comprise less than 0.4 wt %, specifically, less than or equal to 0.3 wt %, or 0 to 0.1 wt % of methanol. The acetone product stream 231 can comprise less than or equal to 150 ppm, or 0 to 100 ppm of methanol. The acetone product stream 231 can comprise greater than or equal to 10 ppm, or greater than or equal to 50 ppm of methanol.

The acetone purification section 200 can provide the acetone purification recycle stream 252 comprising phenol which can be combined with the feed stream 301, combined with the splitter inlet stream 303, sent to a separate process, or a combination including at least one of the foregoing.

Referring back to the phenol purification section, splitter bottom outlet stream 322 can be recovered from the bottom of the splitter column 320. The splitter bottom outlet stream 322 can comprise lower volatility species of the splitter inlet stream 303 including phenol. The splitter bottom outlet stream 322 can comprise greater than or equal to 94 wt %, specifically, 95 to 99 wt %, more specifically, 97 to 99 wt % of phenol. The splitter bottom outlet stream 322 can comprise 0 to 4 wt % of α-methylstyrene. The splitter bottom outlet stream 322 can comprise 0 to 2 wt % of acetophenone.

The splitter bottom outlet stream 322 can comprise 0 to 1 wt % of each of the following independently: acetone, cumene, α-methylstyrene, water, dimethylbenzyl alcohol, paracumyl phenol, dicumyl phenol, hydroxyacetone, acetophenone, methanol, acetaldehyde, 2-methylbenzofuran, and AMS dimers. The splitter bottom outlet stream 322 can be fed to a crude phenol column 360 where it can be separated into a crude top outlet stream 361 and a crude bottom outlet stream 362. The crude phenol column inlet stream can include the splitter bottom outlet stream 322, an optional finisher bottom outlet stream 382, or a combination including at least one of the foregoing. The crude phenol column 360 can operate at a temperature of 100 to 300° C., specifically, 150 to 250° C. The crude phenol column 360 can operate at a pressure of 75 to 275 kPa, specifically, 100 to 225 kPa.

The crude phenol column 360 can include a distillation column which can separate species present in the splitter bottom outlet stream 322 based on their volatility. The crude bottom outlet stream 362 can include lower volatility species present in the splitter bottom outlet stream 322 such as paracumyl phenol, dicumyl phenol, AP, AMS dimer, or a combination comprising at least one of the foregoing. For example, the crude bottom outlet stream 362 can contain dimethylbenzyl alcohol, acetophenone, AMS dimers, dicumyl phenol, paracumyl phenol (PCP), or a combination comprising at least one of the foregoing. The crude bottom outlet stream 362 can be recovered from the phenol purification system 300 for separate processing. The crude top outlet stream 361 can comprise 97 to 99.7 wt % of phenol.

The crude top outlet stream 361 can be fed to an extractor inlet of a hydro-extractor column 370. Water stream 373 containing water can be fed directly to the hydro-extractor column 370 or to a cooler 374 in fluid communication with the hydro-extractor column 370. The hydro-extractor column 370 can include a liquid-liquid extraction device, which can separate compounds based on their relative solubilities in two different immiscible liquid phases. Non-phenol compounds present in one liquid phase (e.g., a phenol rich phase) can be extracted to a second liquid phase (e.g., a water phase) where the non-phenol compound has a greater solubility. Water stream 373 can be used to extract non-phenol compound (e.g., alkylated benzenes) present in the crude top outlet stream 361.

The hydro-extractor column 370 can include internal structures to increase the interfacial area between the two liquid phases. These internal structures can include fixed plates, packing, or a combination including at least one of the foregoing. The hydro-extractor column 370 can be heated (e.g., through a heat exchanger in thermal communication with the hydro-extractor column 370). The hydro-extractor can operate in any suitable flow configuration such that interaction between the two immiscible liquid phases is ensured. For example, heat supplied to the hydro-extractor can buoy the water phase and drive counter-current flow of the two liquid phases within the hydro-extractor, where the phenol rich phase moves toward the bottom of the hydro-extractor while the water phase moves towards the top. The water phase can be cooled in the cooler 374 and returned to the hydro-extractor. The hydro-extractor column 370 can operate at a temperature of 30 to 100° C., specifically, 50 to 70° C. The hydro-extractor column 370 can operate at a pressure of 350 to 550 kPa, specifically, 400 to 500 kPa. At least a portion of the top stream exiting the hydro-extractor column 370 can be removed from the system, for example, upstream of or downstream of the cooler 374 and can optionally be recycled to an upstream unit such as one or both of splitter column 320 or crude phenol column 360.

The extractor primary outlet stream 371 can include the phenol rich phase including phenol and non-phenol compounds (e.g., dicumyl phenol, 2-methylbenzofuran (2-MBF), AP, or a combination comprising at least one of the foregoing). The extractor primary outlet stream 371 can comprise 98 to 99.999 wt % of phenol. Non-phenol compounds present in the extractor primary outlet stream 371 can include heteroatoms (e.g., 2-MBF) which can be alkylated to higher molecular mass species (e.g., greater molecular mass in comparison to the species having the heteroatom) in an optional ion exchanger 375. The effluent from the optional ion exchanger 375 can be fed along a finisher inlet stream 376 to a finishing column 380. The finishing column 380 can separate the finisher inlet stream 376 into a product phenol outlet stream 381 and a finisher bottom outlet stream 382. The finisher bottom outlet stream 382 can optionally be recycled and combined with the splitter bottom outlet stream 322. The finisher column 380 can include at least one distillation column. The product phenol outlet stream 381 can be recovered from the phenol purification system 300 and used in the manufacture of bisphenol-A (BPA) in a BPA production plant. The product phenol outlet stream 381 can comprise greater than or equal to 99.5 wt %, specifically, 99.5 to less than 100 wt % of phenol.

Figure 2:
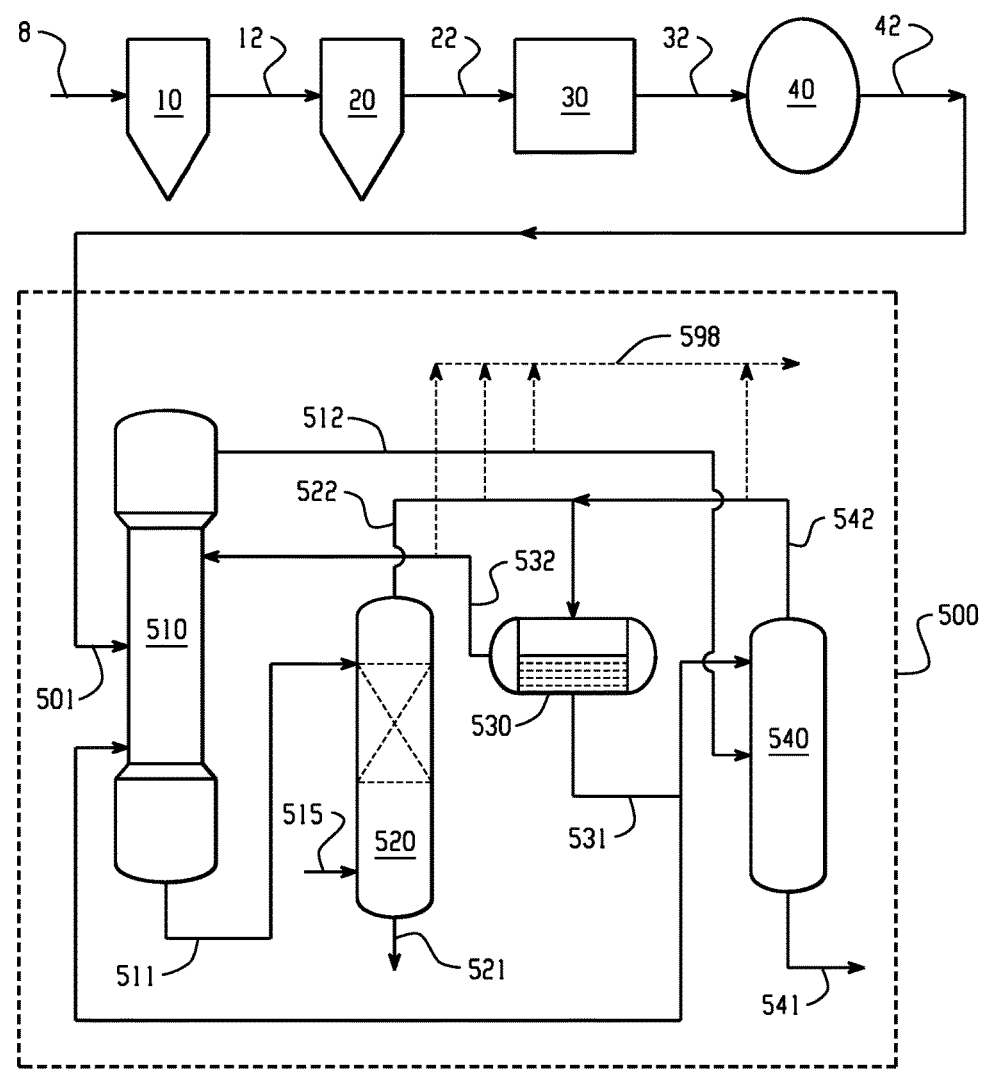
FIG. 2 is a schematic illustration of a bisphenol A production facility comprising an acetone purification system.

A bisphenol A production facility is illustrated in FIG. 2. FIG. 2 illustrates that reactor feed stream 8 can be directed to the BPA reactor 10 to form BPA stream 12. Reactor feed stream 8 can comprise phenol, acetone, and optionally a promoter. The catalyst can be a fixed bed reactor comprising a catalyst. The catalyst can comprise an ion exchange resin (such as a tert-amine divinylbenzene/styrene ion exchange copolymer). The catalyst can comprise a strong acid catalyst (such as hydrochloric acid), a sulfonic resin and a sulfur containing promoter (such as a mercaptan promoter (such as methyl mercaptan, ethyl mercaptan, 2,2-bis(methylthio)propane, mercaptocarboxylic acid, and 3-mercaptopropionic acid), as well as combinations comprising at least one of the foregoing. The phenol and acetone can be present in a molar ratio of 2:1 to 5:1. Reactor feed stream 8 can comprise 75 to 95 wt % phenol and 3 to 25 wt % acetone. The phenol and acetone can be combined in a formulation tank located upstream of BPA reactor 10. BPA stream 12 can be removed from BPA reactor 10. BPA stream 12 can comprise 10 to 50 wt % of bisphenol A.

BPA stream 12 can be directed to crystallization unit 20 to form BPA crystals comprising, for example, one or both of crystalline BPA and an adduct of BPA and phenol. It is noted that "adduct" as used herein refers to the physical association of BPA and phenol (e.g., one molecule of BPA and one molecule of phenol can crystallize together to form a 1:1 molar ratio of BPA/phenol adduct). The crystallization can occur via cooling of the BPA stream. Water can be added to the crystallization unit 20 to increase the rate of the crystallization. The water can be present in BPA stream 12 in an amount of less than or equal to 3 wt %, specifically, 0.1 to 3 wt %. The crystals can be separated by removing the solid portion from the crystallization unit comprising the crystals, for example, via filtration, to form crystallized stream 22.

Crystallized stream 22 can be directed to melting unit 30. The melting unit 30 can melt the crystals, for example, by heating the crystals at a temperature greater than or equal to the crystallization temperature. An additional amount of phenol can be added to the crystallized stream 22 to facilitate the melting of the crystals at a lower temperature. The temperature of the melting unit 30 can be 70 to 100° C., specifically, 75 to 90° C. The crystals can be melted in melting unit 30 to form a melt comprising bisphenol A and phenol. When the melt comprises sulfur, then a base (such as sodium hydroxide and potassium hydroxide) can be added to the melt to form a melt stream with a reduced sulfur content. Melted stream 32 can be directed to filter 40 to form a bisphenol A stream (not shown) and filtered stream 42 comprising 60 to 90 wt % phenol, 5 to 20 wt % bisphenol A, and 5 to 20 wt % water. Filter 40 can comprise a rotary vacuum filter. The bisphenol A stream can be further purified to produce a product bisphenol A. The product bisphenol A can be solidified, for example, in a flaking unit, not shown in FIG. 2.

Filtered stream 42 can be in fluid communication with an acetone purification system 500 of the BPA production plant as extraction stream 501. The acetone purification system 500 can include acetone extraction column 510, which can separate extraction stream 501 into extraction bottom outlet stream 511 and extraction top outlet stream 512. Extraction bottom outlet stream 511 can comprise a solvent, acetone, and water. The solvent can comprise a ketone, an alcohol, an ether, an amide, a hydrocarbon, or a combination comprising at least one of the foregoing. Extraction bottom outlet stream 511 and steam stream 515 can be added to acetone stripper column 520 to form stripper bottom outlet stream 521 and stripper top outlet stream 522. Stripper bottom outlet stream 521 can comprise water that can be disposed of, for example, in a process sewer. Stripper top outlet stream 522 can comprise the solvent and acetone.

At least a portion of stripper top outlet stream 522 can be added to decanter 530 to form aqueous decanter stream 532 and organic decanter stream 531. At least a portion of aqueous decanter stream 532 can be added to acetone extraction column 510 for further purification. Organic decanter stream 531 can be added to one or both of acetone extraction column 510 and solvent recovery column 540. Solvent recovery column 540 can form recovery bottom outlet stream 541 and recovery top outlet stream 542. Recovery bottom outlet stream 541 can be sent to a further purification column to recover any remaining solvent. At least a portion of recovery top outlet stream 542 can be added to decanter 530.

BPA plant acetone recovery stream 598 can comprise at least a portion of one or more of aqueous decanter stream 532, stripper top outlet stream 522, extraction top outlet stream 512, and recovery top outlet stream 542. BPA plant acetone recovery stream 598 can comprise at least a portion of one or more of aqueous decanter stream 532, extraction top outlet stream 512, and recovery top outlet stream 542. BPA plant acetone recovery stream 598 can comprise 98 to 99.6 wt %, specifically, 99 to 99.6 wt % of acetone. BPA plant acetone recovery stream 598 can comprise 0.4 to 2 wt %, specifically, 0.4 to 1 wt % or 1 to 2 wt % of methanol.

The BPA plant acetone recovery stream 598 can be combined with the phenol purification system 300 in a number of locations. The BPA plant acetone recovery stream 598 can be combined with the preheater inlet stream 302, the splitter inlet stream 303, the splitter top outlet stream 321, or a combination comprising at least one of the foregoing.

Combining the BPA plant acetone recovery stream 598 and the preheater inlet stream 302 can allow the streams to equilibrate prior to entering the splitter column 320. It is noted that if the BPA plant acetone recovery stream 598 is added to the preheater 310 a water removal stream 510 can be added to remove an amount of water above an equilibrium amount. The preheater 310 can be a more efficient heat transfer device in comparison to the splitter column 320 (e.g., owed to lower heat loss, lower thermal resistance of the material of construction, or flow configuration), or the opposite can be the case. Thus, selecting between the preheater inlet stream 302 and the splitter inlet stream 303, or selecting how much of the BPA plant acetone recovery stream 598 is supplied to either location, can be influenced by heat transfer efficiency differences between the preheater 310 and the splitter column 320. Adding the BPA plant acetone recovery stream 598 upstream of splitter column 320 allows for heavy impurities to be removed via splitter bottom outlet stream 322.

BPA plant acetone recovery stream 598 can be added to splitter top outlet stream 321. Such an addition can avoid potential interactions with the phenol of the phenol purification system. When the BPA plant acetone recovery stream 598 is added to splitter top outlet stream 321 heavy impurities can be removed via second bottom stream 232.

The method of recovering acetone in a BPA production plant can be done in a recovery system. For example, the system can comprise a phenol purification system 300 that purifies phenol produced in a phenol production facility and a BPA phenol purification system 400 of a bisphenol A production plant. The phenol purification system 300 can comprise a preheater 310, a splitter column 320, a crude phenol column 360, a hydro-extractor column 370, an optional ion exchanger 375, and a finishing column 380. The preheater 310 can comprise a preheater inlet and a preheater outlet. The splitter column 320 can comprise a splitter inlet in fluid communication with the preheater outlet, a splitter top outlet, and a splitter bottom outlet. The crude phenol column 360 can comprise a crude inlet in fluid communication with the splitter bottom outlet, a crude top outlet, and a crude bottom outlet. The hydro-extractor column 370 can comprise an extractor inlet in fluid communication with the crude top outlet, an extractor outlet, and an extractor primary outlet. The hydro-extractor column 370 can comprise a cooler extractor inlet that can be in fluid communication with a cooler outlet of a cooler 374. The cooler 374 can further comprise a cooler inlet in fluid communication with the extractor outlet. The finishing column 380 can comprise a finisher inlet in fluid communication with the extractor primary outlet, a product phenol outlet, and a finisher bottom outlet. The finisher bottom outlet can optionally be in fluid communication with the crude inlet. The system can optionally comprise an optional ion exchanger 375 comprising an exchanger inlet in fluid communication with the extractor primary outlet and an exchanger outlet in fluid communication with the finisher inlet.

The acetone purification system 200 can comprise first acetone column 210, second acetone column 230, and separator 250. First acetone column 210 can comprise a first acetone inlet, a first acetone top outlet, and a first acetone bottom outlet. Second acetone column 230 can comprise a second acetone inlet, a second acetone top outlet, and a second acetone bottom outlet. Separator 250 can comprise a separator inlet, a separator top outlet, and a separator bottom outlet. The first acetone inlet can be in fluid communication with the splitter top outlet and optionally with an outlet of the acetone purification system 500 of the BPA production facility. The first acetone bottom outlet can be in fluid communication with the second acetone inlet. The second acetone bottom outlet can be in fluid communication with the separator inlet. The separator bottom outlet can be in fluid communication with the preheater inlet.

The acetone purification system 500 can comprise acetone extraction column 510, acetone stripper column 520, decanter 530, and solvent recovery column 540. Acetone extraction column 510 can comprise a first extraction inlet, an optional second extraction inlet, a third extraction inlet, a top extraction outlet, and a bottom extraction outlet. Acetone stripper column 520 can comprise a stripper inlet, a steam stripper inlet, a top stripper outlet, and a bottom stripper outlet. Decanter 530 can comprise a decanter inlet, an aqueous decanter outlet, and an organic decanter outlet. Solvent recovery column 540 can comprise a first solvent recovery inlet, a second solvent recovery inlet, a top solvent recovery outlet, and a bottom recovery outlet. The top extraction outlet can be in fluid communication with the first solvent recovery inlet. The top solvent recovery outlet can be in fluid communication with the decanter inlet. The organic decanter outlet can be in fluid communication with one or both of the second solvent recovery inlet and the optional second extraction inlet. The aqueous decanter outlet can be in fluid communication with the third extraction inlet. The bottom extraction outlet can be in fluid communication with the stripper inlet. The top stripper outlet can be in fluid communication with the decanter inlet.

For acetone recovery, the top extraction outlet, the top stripper outlet, the aqueous decanter outlet, top solvent recovery outlet, or a combination comprising at least one of the foregoing of the acetone purification system 500 can be in fluid communication with the preheater inlet of the preheater 310, the splitter inlet of the splitter column 320, the first acetone inlet of first acetone column 210, or a combination comprising at least one of the foregoing.

Set forth below are some non-limiting embodiments of the present disclosure.

Embodiment 1

A method of recovering acetone comprising: reacting phenol and acetone in the presence of a catalyst in a BPA reactor to produce a bisphenol A stream comprising bisphenol A; separating the bisphenol A stream into a product bisphenol A stream and an extraction stream comprising an unreacted acetone; separating the extraction stream into an extraction top outlet stream and an extraction bottom outlet stream in an acetone extraction column; separating the extraction bottom outlet stream in an acetone stripper column in the presence of steam to form a stripper top outlet stream and a stripper bottom outlet stream comprising water; separating the extraction top outlet stream in a solvent recovery column to form a recovery top outlet stream and a recovery bottom outlet stream; separating one or both of the recovery top outlet stream and the stripper top outlet stream in a decanter to form an organic decanter stream and an aqueous decanter stream; forming a bisphenol A plant acetone recovery stream comprising at least a portion of one or more of the extraction top outlet stream, the stripper top outlet stream, the aqueous decanter stream, and the recovery top outlet stream; introducing the bisphenol A plant acetone recovery stream to a phenol purification plant, wherein the bisphenol A plant acetone recovery stream comprises methanol and a recovered acetone; and purifying the bisphenol A plant acetone recovery stream to form an acetone product stream comprising a purified acetone.

Embodiment 2

The method of Embodiment 1, wherein the methanol is present in the bisphenol A plant acetone recovery stream in an amount of 0.4 to 2 wt % based on the total weight of the bisphenol A plant acetone recovery stream.

Embodiment 3

The method of any one of the preceding embodiments, wherein the acetone product stream comprises less than or equal to 0.3 wt % of methanol, or less than or equal to 150 ppm of methanol based on the total weight of the acetone product stream.

Embodiment 4

The method of Embodiment 3, wherein the acetone product stream comprises greater than or equal to 10 ppm of methanol based on the total weight of the acetone product stream.

Embodiment 5

The method of any one of the preceding embodiments, further comprising directing at least a portion of the aqueous decanter stream to the acetone extraction column.

Embodiment 6

The method of any one of the preceding embodiments, further comprising directing at least a portion of the organic decanter stream to one or both of the solvent recovery column and the acetone extraction column.

Embodiment 7

The method of any one of the preceding embodiments, wherein the reacting phenol and acetone comprises directing a reactor feed stream comprising the phenol and the acetone to the BPA reactor and forming a BPA stream; directing the BPA stream to a crystallization unit to form a crystallized stream comprising BPA crystals; directing the crystallized stream to a melting unit to form a melted stream comprising bisphenol A and phenol; directing the melted stream to a filter to form the product bisphenol A stream and a filtered stream; wherein the extraction stream comprises the filtered stream.

Embodiment 8

The method of any one of the preceding embodiments, wherein the bisphenol A plant acetone recovery stream comprises at least a portion of one or more of the aqueous decanter stream, the extraction top outlet stream, and the recovery top outlet stream.

Embodiment 9

The method of any one of the preceding embodiments, wherein the introducing the bisphenol A plant acetone recovery stream to the phenol purification plant comprises introducing the bisphenol A plant acetone recovery stream to at least one of a preheater, a splitter column, and a first acetone column; and wherein the purifying comprises heating a preheater inlet stream comprising cumene, phenol, and acetone in the preheater to form the splitter inlet stream; separating a splitter inlet stream comprising the cumene, the phenol, and the acetone into a splitter top outlet stream comprising the acetone and the cumene and a splitter bottom outlet stream comprising the phenol in the splitter column; separating the splitter top outlet stream in the first acetone column into a first top stream and a first bottom stream; and separating the first bottom stream in a second acetone column into a second bottom stream and the acetone product stream.

Embodiment 10

The method of Embodiment 9, wherein the introducing the bisphenol A plant acetone recovery stream comprises introducing the bisphenol A plant acetone recovery stream to the preheater inlet stream.

Embodiment 11

The method of Embodiment 10, further comprising adding a water removal stream to the preheater of the phenol purification plant.

Embodiment 12

The method of any one of Embodiments 9-11, wherein the introducing the bisphenol A plant acetone recovery stream comprises combining the bisphenol A plant acetone recovery stream with the splitter inlet stream.

Embodiment 13

The method of any one of Embodiments 9-12, wherein the introducing the bisphenol A plant acetone recovery stream comprises combining the bisphenol A plant acetone recovery stream with the splitter top outlet stream.

Embodiment 14

The method of any one of Embodiments 9-13, further comprising separating the second bottom stream in a separator into a decanted stream and an acetone purification recycle stream.

Embodiment 15

The method of Embodiment 14, further comprising adding the acetone purification recycle stream to the preheater inlet stream.

Embodiment 16

The method of any one of Embodiments 14-15, further comprising adding the acetone purification recycle stream to the splitter inlet stream.

Embodiment 17

The method of any one of Embodiments 9-16, further comprising purifying the splitter bottom outlet stream to form a product phenol outlet stream.

Embodiment 18

The method of any one of the preceding embodiments, further comprising introducing the acetone product stream to the BPA reactor.

Embodiment 19

A method of purifying a recovered acetone comprising: introducing a bisphenol A plant acetone recovery stream, preferably, the bisphenol A plant acetone recovery stream of any one of the preceding embodiments, to at least one of a preheater, a splitter column, and a first acetone column; wherein the bisphenol A plant acetone recovery stream comprises methanol and the recovered acetone; heating a preheater inlet stream comprising cumene, phenol, and acetone in the preheater to form a splitter inlet stream; separating the splitter inlet stream comprising the cumene, the phenol, and the acetone into a splitter top outlet stream comprising the acetone and the cumene and a splitter bottom outlet stream comprising the phenol in the splitter column; separating the splitter top outlet stream in the first acetone column into a first top stream and a first bottom stream; separating the first bottom stream in a second acetone column into a second bottom stream and an acetone product stream comprising a purified acetone.

Embodiment 20

An integrated system for purifying acetone, comprising: an acetone extraction column comprising a first extraction inlet, a top extraction outlet, and a bottom extraction outlet; an acetone stripper column comprising comprise a stripper inlet, a steam stripper inlet, a top stripper outlet, and a bottom stripper outlet; wherein the bottom extraction outlet is in fluid communication with the stripper inlet; a decanter comprising a decanter inlet, an aqueous decanter outlet, and an organic decanter outlet; wherein one or both of the top solvent recovery outlet and the top stripper outlet is in fluid communication with the decanter inlet; and an optional solvent recovery column comprising a first solvent recovery inlet, a second solvent recovery inlet, a top solvent recovery outlet, and a bottom recovery outlet; wherein, if present, the top extraction outlet is in fluid communication with the first solvent recovery inlet; the organic decanter outlet is in fluid communication with one or both of the second solvent recovery inlet and a second extraction inlet of the acetone extraction column; and wherein the top extraction outlet, the top stripper outlet, the aqueous decanter outlet, top solvent recovery outlet, or a combination comprising at least one of the foregoing is in fluid communication with a stream of a phenol purification system; wherein the phenol purification system is configured to recover an acetone product stream.

Embodiment 21

The integrated system of Embodiment 20, further comprising a bisphenol A reactor in fluid communication with a crystallization unit that is in fluid communication with a melting unit that is in fluid communication with a filter; wherein the filter is in fluid communication with the first extraction inlet of the acetone extraction column.

Embodiment 22

The integrated system of any one of Embodiments 20-21, wherein the top stripper outlet, the aqueous decanter outlet, top solvent recovery outlet, or a combination comprising at least one of the foregoing is in fluid communication with the phenol purification system.

Embodiment 23

The integrated system of any one of Embodiments 20-22, wherein the phenol purification system comprises a preheater comprising a preheater inlet and a preheater outlet; and a splitter column comprising a splitter inlet in fluid communication with the preheater outlet, a splitter top outlet, and a splitter bottom outlet; a first acetone column comprising a first acetone inlet, a first acetone top outlet, and a first acetone bottom outlet; wherein the splitter top outlet is in fluid communication with the first acetone inlet; and a second acetone column comprising a second acetone inlet, a second acetone top outlet, and a second acetone bottom outlet; wherein the first acetone bottom outlet is in fluid communication with the second acetone inlet; and wherein the top extraction outlet, the top stripper outlet, the aqueous decanter outlet, top solvent recovery outlet, or a combination comprising at least one of the foregoing is in fluid communication with the preheater inlet, the splitter inlet, the first acetone inlet, or a combination comprising at least one of the foregoing.

Embodiment 24

The integrated system of Embodiment 23, wherein the top extraction outlet, the top stripper outlet, the aqueous decanter outlet, top solvent recovery outlet, or a combination comprising at least one of the foregoing is in fluid communication with the preheater inlet.

Embodiment 25

The integrated system of any one of Embodiments 23-24, wherein the top extraction outlet, the top stripper outlet, the aqueous decanter outlet, top solvent recovery outlet, or a combination comprising at least one of the foregoing is in fluid communication with the splitter inlet.

Embodiment 26

The integrated system of any one of Embodiments 23-25, wherein the top extraction outlet, the top stripper outlet, the aqueous decanter outlet, top solvent recovery outlet, or a combination comprising at least one of the foregoing is in fluid communication with the first acetone inlet.

Embodiment 27

The integrated system of any one of Embodiments 20-26, wherein the phenol purification system is configured to recover the acetone product stream such that the acetone product stream comprises less than or equal to 0.3 wt % of methanol or less than or equal to 150 ppm of methanol based on the total weight of the acetone product stream.

Embodiment 28

The integrated system of Embodiment 27, wherein the acetone product stream comprises greater than or equal to 10 ppm of methanol based on the total weight of the acetone product stream.

Embodiment 29

The integrated system of any one of Embodiments 20-28, further comprising a bisphenol A reactor that is in fluid communication with the acetone extraction column; and wherein the acetone product stream is in fluid communication with the BPA reactor.

Embodiment 30

Use of a phenol purification plant in purifying a bisphenol A plant acetone recovery stream from a bisphenol A plant, preferably, the phenol purification plant and the bisphenol A plant acetone recovery stream are each independently one of those described in any one of the foregoing embodiments.

Although the description of the process is directed to a continuous process, any one or more of the steps can be conducted batch-wise.

Unless specifically stated otherwise, the weight percent values used herein are based on the total weight of the respective stream.

It will be appreciated by persons skilled in the art that the positioning of the various streams/lines as described herein as being, e.g., in the "top", "middle", "bottom", or "side" of a particular vessel (such as an acid-cracker, distillation column, extraction column, and the like) is relative because the actual position at which material is to be introduced or recovered is dependent on the conditions being maintained in the particular unit. For example, a stream entering the "bottom" of a column can actually enter several stages above the sump including the reboiler of the column, and a stream exiting the "top" of the column can actually exit several stages below the top stage including the condenser of the column. Thus, such terms herein are included for ease of reference to describe a general orientation regarding various columns and lines/streams and such terms are not meant to be limiting to one exact location. Also, although for illustrative purposes, the accompanying figures depict singular units, it is understood that multiple vessels can be used where suitable. Furthermore, multiple vessels can have any suitable flow arrangement such as serial, parallel, or a combination including at least one of the foregoing. Further still, while the figures and text often refer to combining streams upstream of a unit, they can likewise be entered directly into the unit.

In general, the disclosure can alternately comprise, consist of, or consist essentially of, any appropriate components herein disclosed. The disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this disclosure belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

In addition, it is to be understood that the described elements can be combined in any suitable manner in the various embodiments.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

We claim:

1. A method of recovering acetone comprising:
   reacting phenol and acetone in the presence of a catalyst in a bisphenol A reactor to produce a bisphenol A stream comprising bisphenol A;
   separating the bisphenol A stream into a product bisphenol A stream and an extraction streamcomprising an unreacted acetone;
   separating the extraction stream into an extraction top outlet stream and an extraction bottom outlet stream in an acetone extraction column;
   separating the extraction bottom outlet stream in an acetone stripper column in the presence of steam to form a stripper top outlet stream and a stripper bottom outlet stream comprising water;
   separating the extraction top outlet stream in a solvent recovery column to form a recovery top outlet stream and a recovery bottom outlet stream;
   separating one or both of the recovery top outlet stream and the stripper top outlet stream in a decanter to form an organic decanter stream and an aqueous decanter stream;
   forming a bisphenol A plant acetone recovery stream comprising at least a portion of one or more of the extraction top outlet stream, the stripper top outlet stream, the aqueous decanter stream, and the recovery top outlet stream;
   introducing the bisphenol A plant acetone recovery stream to a phenol purification plant, wherein the bisphenol A plant acetone recovery stream comprises methanol and a recovered acetone; and
   purifying the bisphenol A plant acetone recovery stream to form an acetone product stream.

2. The method of claim 1, wherein the methanol is present in the bisphenol A plant acetone recovery stream in an amount of 0.4 to 2 wt % based on the total weight of the bisphenol A plant acetone recovery stream.

3. The method of claim 1, wherein the acetone product stream comprises less than or equal to 0.3 wt % of methanol.

4. The method of claim 1, wherein the acetone product stream comprises or less than or equal to 150 ppm of methanol based on the total weight of the acetone product stream.

5. The method of claim 3, wherein the acetone product stream comprises greater than or equal to 10 ppm of methanol based on the total weight of the acetone product stream.

6. The method of claim 1, wherein the bisphenol A plant acetone recovery stream comprises at least a portion of one or more of the aqueous decanter stream, the extraction top outlet stream, and the recovery top outlet stream.

7. The method of claim 1, wherein the introducing the bisphenol A plant acetone recovery stream to the phenol purification plant comprises introducing the bisphenol A plant acetone recovery stream to at least one of a preheater, a splitter column, and a first acetone column; and
   wherein the purifying comprises
      heating a preheater inlet stream comprising cumene, phenol, and acetone in the preheater to form the splitter inlet stream;
      separating a splitter inlet stream comprising the cumene, the phenol, and the acetone into a splitter top outlet stream comprising the acetone and the cumene and a splitter bottom outlet stream comprising the phenol in the splitter column;
      separating the splitter top outlet stream in the first acetone column into a first top stream and a first bottom stream; and
      separating the first bottom stream in a second acetone column into a second bottom stream and the acetone product stream.

8. The method of claim 7, wherein the introducing the bisphenol A plant acetone recovery stream comprises introducing the bisphenol A plant acetone recovery stream to the preheater inlet stream.

9. The method of claim 7, wherein the introducing the bisphenol A plant acetone recovery stream comprises introducing the bisphenol A plant acetone recovery stream to the splitter inlet stream.

10. The method of claim 7, wherein the introducing the bisphenol A plant acetone recovery stream comprises introducing the bisphenol A plant acetone recovery stream to the splitter top outlet stream.

11. The method of claim 1, further comprising introducing the acetone product stream to the bisphenol A reactor.

12. A method of purifying a recovered acetone comprising:
   introducing a bisphenol A plant acetone recovery stream, preferably, the bisphenol A plant acetone recovery stream of any one of the preceding claims, to at least one of a preheater, a splitter column, and a first acetone column of a phenol purification plant; wherein the bisphenol A plant acetone recovery stream comprises methanol and the recovered acetone;
   heating a preheater inlet stream comprising cumene, phenol, and acetone in the preheater to form a splitter inlet stream;
   separating the splitter inlet stream comprising the cumene, the phenol, and the acetone into a splitter top outlet stream comprising the acetone and the cumene and a splitter bottom outlet stream comprising the phenol in the splitter column;
   separating the splitter top outlet stream in the first acetone column into a first top stream and a first bottom stream;
   separating the first bottom stream in a second acetone column into a second bottom stream and an acetone product stream comprising a purified acetone.

13. An integrated system for purifying acetone, comprising:
   an acetone extraction column comprising a first extraction inlet, a top extraction outlet, and a bottom extraction outlet;
   an acetone stripper column comprising comprise a stripper inlet, a steam stripper inlet, a top stripper outlet, and a bottom stripper outlet; wherein the bottom extraction outlet is in fluid communication with the stripper inlet;

a decanter comprising a decanter inlet, an aqueous decanter outlet, and an organic decanter outlet; wherein one or both of the top solvent recovery outlet and the top stripper outlet is in fluid communication with the decanter inlet; and an optional solvent recovery column comprising a first solvent recovery inlet, a second solvent recovery inlet, a top solvent recovery outlet, and a bottom recovery outlet; wherein, if present, the top extraction outlet is in fluid communication with the first solvent recovery inlet; the organic decanter outlet is in fluid communication with one or both of the second solvent recovery inlet and a second extraction inlet of the acetone extraction column; and wherein the top extraction outlet, the top stripper outlet, the aqueous decanter outlet, top solvent recovery outlet, or a combination comprising at least one of the foregoing is in fluid communication with a stream of a phenol purification system; wherein the phenol purification system is configured to recover an acetone product stream.

14. The integrated system of claim 13, wherein the top stripper outlet, the aqueous decanter outlet, top solvent recovery outlet, or a combination comprising at least one of the foregoing is in fluid communication with the phenol purification system.

15. The integrated system of claim 13, wherein the phenol purification system comprises a preheater comprising a preheater inlet and a preheater outlet; and a splitter column comprising a splitter inlet in fluid communication with the preheater outlet, a splitter top outlet, and a splitter bottom outlet;

a first acetone column comprising a first acetone inlet, a first acetone top outlet, and a first acetone bottom outlet; wherein the splitter top outlet is in fluid communication with the first acetone inlet; and a second acetone column comprising a second acetone inlet, a second acetone top outlet, and a second acetone bottom outlet; wherein the first acetone bottom outlet is in fluid communication with the second acetone inlet; and wherein the top extraction outlet, the top stripper outlet, the aqueous decanter outlet, top solvent recovery outlet, or a combination comprising at least one of the foregoing of the is in fluid communication with the preheater inlet, the splitter inlet, the first acetone inlet, or a combination comprising at least one of the foregoing.

16. The integrated system of claim 15, wherein the top extraction outlet, the top stripper outlet, the aqueous decanter outlet, top solvent recovery outlet, or a combination comprising at least one of the foregoing is in fluid communication with one or more of the preheater inlet, the splitter inlet, and the first acetone inlet.

17. The integrated system of claim 13, wherein the phenol purification system is configured to recover the acetone product stream such that the acetone product stream comprises less than or equal to 0.3 wt % of methanol or less than or equal to 150 ppm of methanol based on the total weight of the acetone product stream.

18. The integrated system of claim 17, wherein the phenol purification system is configured to recover the acetone product stream such that the acetone product stream comprises greater than or equal to 10 ppm of methanol based on the total weight of the acetone product stream.

19. The integrated system of claim 13, further comprising a bisphenol A reactor that is in fluid communication with the acetone extraction column; and wherein the acetone product stream is in fluid communication with the BPA reactor.

* * * * *